United States Patent
Sato

[19]

[11] Patent Number: 6,061,425
[45] Date of Patent: May 9, 2000

[54] COATING THICKNESS GAUGE BY X-RAY FLUORESCENCE

[75] Inventor: Masao Sato, Tokyo, Japan

[73] Assignee: Seiko Instruments, Inc., Tokyo, Japan

[21] Appl. No.: 08/194,369

[22] Filed: Feb. 9, 1994

[30] Foreign Application Priority Data

Feb. 9, 1993 [JP] Japan .................................. 5-021234

[51] Int. Cl.[7] ................................................ G01N 23/223
[52] U.S. Cl. ................................................ 378/50; 378/44
[58] Field of Search .................................................. 378/50

[56] References Cited

U.S. PATENT DOCUMENTS 4,959,848   9/1990   Parobek ...................................... 378/50

*Primary Examiner*—Craig E. Church
*Attorney, Agent, or Firm*—Loeb & Loeb LLP

[57] ABSTRACT

In order to automatically measure the thickness of coatings on a sample, a plurality of calibration curves are stored in a memory circuit beforehand, and X-ray fluorescence generated by irradiation of the sample with primary X-rays is detected by an X-ray fluorescence coating thickness gauge. The X-ray fluorescence is differentiated according to wavelength (energy) by a differentiating circuit. By this differential manipulation, the materials of a sample are identified. Based on the identified constituents of a sample, automatic selection can be made of the most probable and suitable calibration curve out of the plural number of calibration curves stored in a memory and finally coating thickness can be measured on the basis of the selected calibration curve and the intensity of X-ray fluorescence of the sample obtained by the coating thickness gauge.

5 Claims, 3 Drawing Sheets

COATING THICKNESS GAUGE BY X-RAY FLUORESCENCE

BACKGROUND OF THE INVENTION

This invention relates to an X-ray fluorescence coating thickness gauge which measures the thickness of metal coatings applied to electronic components etc. utilizing X-ray fluorescence.

Coating thickness gauges using X-ray fluorescence in the prior art measure coating thickness by observing the intensity of X-ray fluorescence generated from a test sample in response to irradiation of the coated surface of the sample, which has a coating film with one or a plural of components, with primary X-rays. An example of this procedure is shown in FIG. 2.

At first, a calibration curve is created. For this purpose, a standard sample is prepared as follows. On a base material which is the same as that of a sample to be subsequently measured, coatings of the same material as the sample to be subsequently measured are formed in two or three layers, or levels of thickness. The resulting standard sample is irradiated with primary X-rays and X-ray fluorescence which is generated by the irradiation is measured using an X-ray fluorescence coating thickness gauge. Then, the relations of measured intensity of X-ray fluorescence and coating thickness, which are the calibration curves, are acquired.

In the case where miscellaneous samples are intended to be measured by an X-ray fluorescence coating thickness gauge, the same standard samples with the same materials and the same coating materials as those for which measurement is expected should be made as above, and a plural number of calibration curves are stored in the memory means beforehand. Finally, the calibration curves thereof should be stored in the memory means in the X-ray fluorescence coating thickness gauge (filing of calibration curve data).

Next, test samples are measured. That is, the base materials and coating materials of samples for which coating thickness is to be measured by the gauge is verified (verification of sample ORIG). A calibration curve is selected out of calibration curve data stored and filed in the memory means referring to the same ORIG of the sample.

After setting a sample on the X-ray fluorescence coating thickness gauge X-ray fluorescence is detected by irradiation with the primary X-rays (sample measurement).

The coating thickness of the sample above is acquired referring to the intensity of fluorescence X-ray and the calibration curve which is selected (the measurement result).

In case that coating thickness of a sample is measured by using an X-ray fluorescence coating thickness gauge as explained in above, constituents of the sample should be known beforehand. Selection of the suitable calibration curve applicable for the purpose, out of curves which are organized beforehand, is required.

In case that coating thickness of a sample is to be measured by using an X-ray fluorescence coating thickness gauge, observers have to identify constituents of the sample (those of base materials and/or coating materials) and then to select and to determine a calibration curve out of those filed in the memory means thereof and to measure samples. Every time the constituents of samples to be measured changes, the calibration curve has to be selected again.

SUMMARY OF THE INVENTION

An object of this invention is obviate the inconveniences of the prior art described above and to provide an X-ray fluorescence coating thickness gauge which can measure easily coating thickness of unknown samples in real time, in that right after the detection of the X-ray fluorescence spectrum of a sample to be measured, analysis of the spectrum, identification of constituents of the sample and determination of the constituent information are done and a calibration curve which has the same constituent information as that of the sample is selected from a data file containing a plurality of calibration curves, and finally the coating thickness is determined with reference to the selected calibration curve in relation to the intensity of the detected X-ray fluorescence.

For solving the problems above, an X-ray fluorescence coating thickness gauge according to the present invention comprises memory means which stores multiple calibration curves showing relations between coating thickness and intensity of X-ray fluorescence, the calibration curves being acquired from samples of which constituents and coating thickness are known beforehand, a differentiating circuit which does differential manipulation of the X-ray fluorescence spectrum of a sample, and automatic identification means which automatically identifies constituents of the sample based on the output from the differentiating circuit, and means for selecting the most suitable calibration curve of the stored calibration curves by comparing the identified constituents with constituents used in each of the calibration curves.

X-ray fluorescence is detected, which is generated by the irradiation of a sample with primary X-rays by way of the X-ray fluorescence coating thickness gauge. The X-ray fluorescence is differentiated on the basis of wave length (energy) in the differentiating circuit. By this differential manipulation, the materials of a sample are identified. Although constituents of a sample can be verified and identified through the intensity of X-ray fluorescence itself, automatic identification is difficult because of the influence of background depending on the primary X-ray intensity, etc. But in case of differential manipulation on the basis of wave length by the differentiating circuit in response to detected X-ray fluorescence, the identification of components of a sample can easily be done because the peak is apt to be found and almost without influence of background depending on the primary X-ray intensity. In accordance with the identified constituents of a sample, automatic selection of the most probable and suitable calibration curve out of the plural number of calibration curves stored in memory means can be achieved. Finally, coating thickness can be measured referring to the calibration curve based on the intensity of X-ray fluorescence of a sample obtained by way of the X-ray fluorescence coating thickness gauge.

DESCRIPTION OF THE PREFERRED EMBODIMENTS

Based on FIGS. 1 and 3, an embodiment of this invention will be described herebelow. According to the classification by X-ray spectrum analysis method of an X-ray fluorescence coating thickness gauge, there exists a wave length dispersion system (WDS) to which an analyzing crystal method is applied and an energy dispersion system (EDS) to which an Si (Li) semiconductor detector or proportional counter is applied. Referring to the fact that the EDS method is broadly utilized due to the high efficiency in collimating primary X-rays, an embodiment will be described for the case in which an Si (Li) Semiconductor detector is applied.

The following five kinds of calibration curves may be preliminarily stored in the memory means 12 of the X-ray fluorescence coating thickness gauge: a) gold coated on copper [Au, Cu]; b) Nickel coated on copper [Ni, Cu]; c) gold coated on nickel on copper base [Au, Ni, Cu]; d) solder coated on copper [Sn, Pb, Cu]; and e) silver coated on alloy 42 [Ag, Fe, Ni]. Those calibration curves are acquired by process employed in the prior art, and then are stored and registered into the memory means with corresponding constituent codes (measurement of standard sample, filing of calibration data).

In this particular case, the number of elements and the names thereof are enough for element information.

Figure 1:
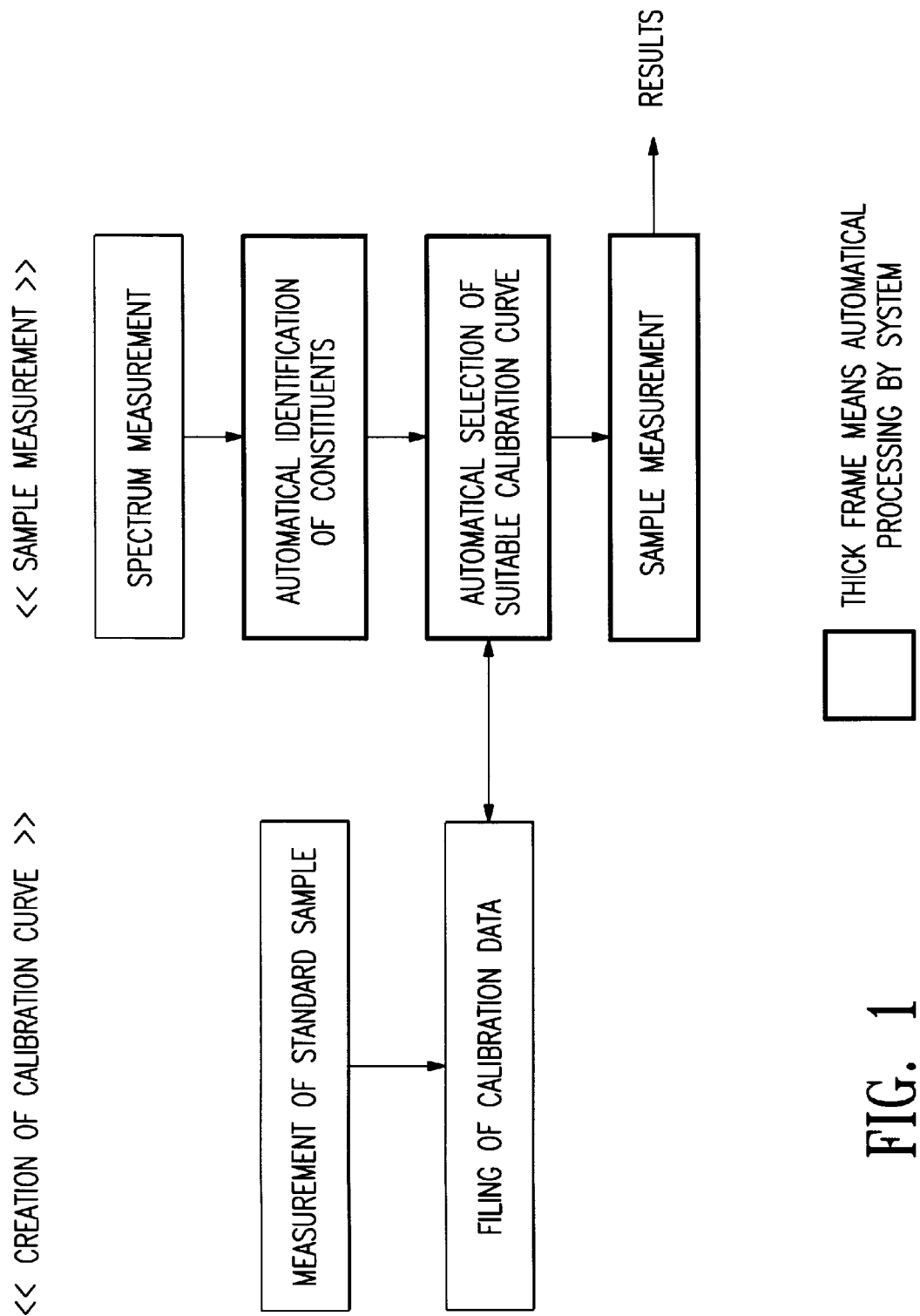
FIG. 1 shows a flow chart of sample measurement with a gauge according to the present invention.
Figure 2:
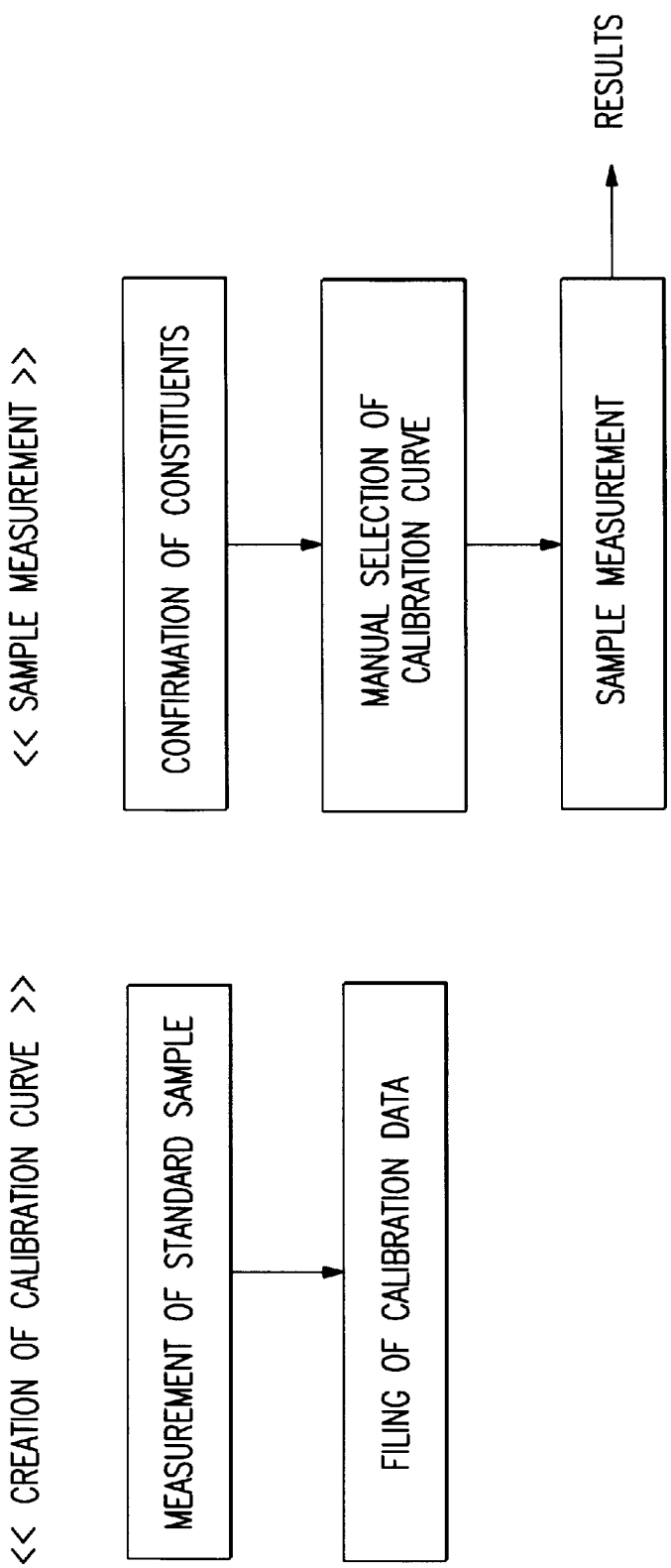
FIG. 2 shows a flow chart of a sample measurement according to the prior art.
Figure 3:
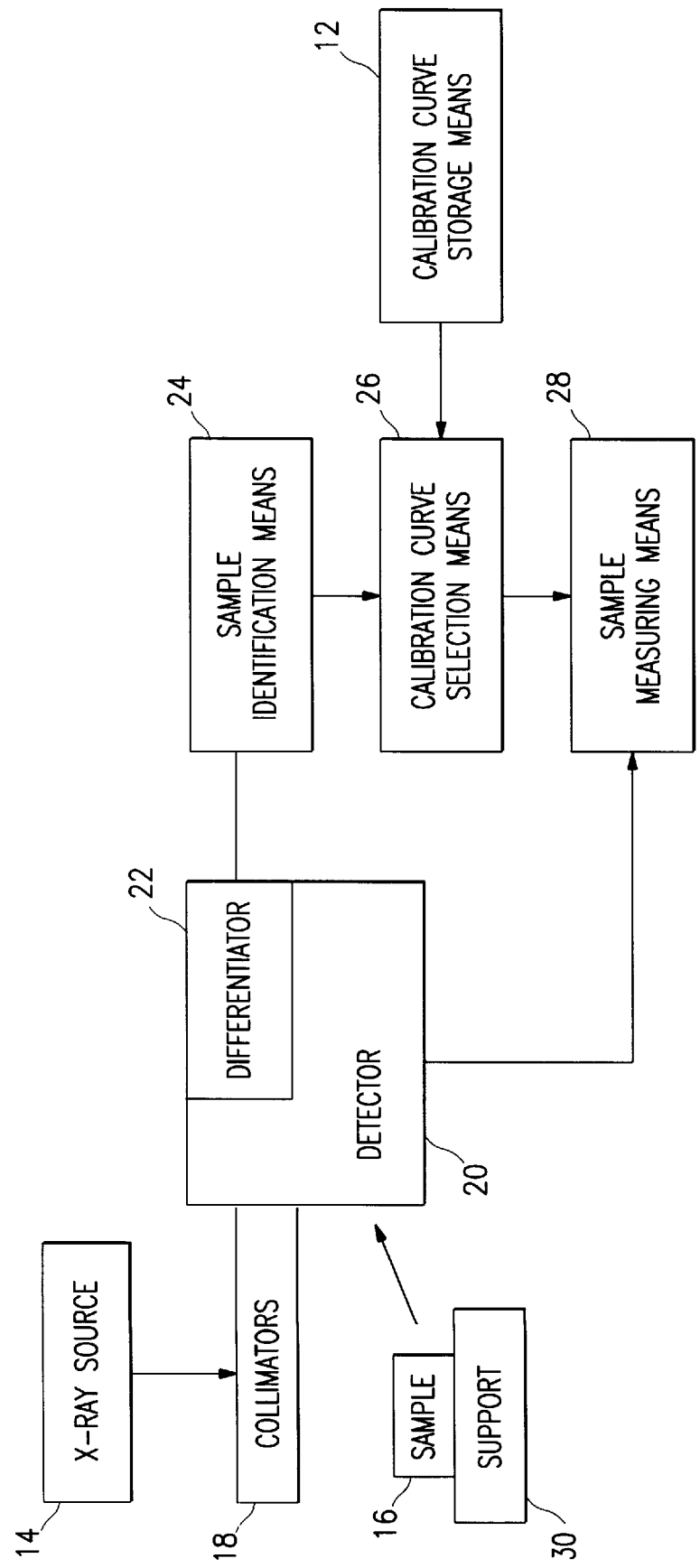
FIG. 3 is a block diagram of one suitable embodiment of a gauge according to the invention.

Referring to FIGS. 1 and 3, before measurement of the coating thickness of an unknown, or test, sample is performed, spectrum measurement of X-ray fluorescence is done for the first several seconds (spectrum measurement). A primary X-ray beam is produced by a source 14 and is focussed on test sample 16 by a collimator 18. X-ray fluorescence is detect by a detector 20 and differential manipulation by the wavelength (energy) of the spectrum is done in a differentiating circuit 22 with which the X-ray fluorescence coating thickness gauge is equipped. After detecting each peak of the spectrum, sample components are automatically identified (automatic identification of constituents) in sample identification means 24. Supposing that the three elements nickel, copper and gold are identified at this time, the third (c)) calibration curve can be selected by a calibration curve selection means 26 out of the file of stored calibration curves since the number of elements and those element names coincide those identified (automatic selection of suitable calibration curve).

Next, the coating thickness of sample 16 is measured according to a conventional X-ray fluorescence coating thickness measuring method (sample measurement) by sample measuring means 28. The X-ray fluorescence coating thickness gauge has a plurality of collimators 18 for focussing the primary X-rays into the requested size, and such gauge is coupled with small and fine electronic parts.

The collimators are selected in one of the following ways.

The first alternative is to execute a preliminary measurement with the smallest collimator size for automatic identification, and then to execute the coating thickness measurement by using the most suitable size of collimator.

The second alternative is to identify automatically by using the most suitable collimator in terms of the X-ray intensity by setting a sample on a table, or support, 30 which is made of a non-metal material and of light elements, etc., such as plastic or other,- and then performing the coating thickness measurement by using the most suitable size of collimator. The merit of the latter is there is no necessity to consider the size of the sample.

The third alternative is to input only collimator size in advance and not only to execute automatic identification but also to measure automatically actual coating thickness, too.

If three elements such as Pd, Ni and Cu are identified as a result of automatic identification, a message is output that no calibration curve has been found in the stored and registered file.

According to this invention, even unknown sample coating thickness can be measured only by initiating the starting of measurement after setting the sample. Therefore operation efficiency is much improved.

This application relates to subject matter disclosed in Japanese Application number 5-21234, filed on Feb. 9, 1993, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. An X-ray fluorescence coating thickness gauge comprising: memory means for storing a plurality of calibration curves, each curve representing a relation between coating thickness and X-ray fluorescence intensity for a respective reference sample having known constituents and coating thickness; means for irradiating a test sample with a primary X-ray beam collimated by a collimator; means for detecting X-ray fluorescence generated from the test sample in response to irradiation by the primary X-ray beam; a differentiating circuit for performing differential manipulation of the X-ray fluorescence spectrum of the test sample based on the X-ray fluorescence detected by said means for detecting and providing an output dependent on constituents of the test sample; automatic identification means coupled to said differentiating circuit for automatically identifying constituents of the test sample based on the output from said differentiating circuit; automatic selecting means coupled to said automatic identification means and to said memory means for selecting from the stored calibration curves the calibration curve associated with constituents which correspond most closely to the constituents identified by said automatic identification means by comparing the constituents identified by said automatic identification means with constituents associated with each of the calibration curves; and means coupled to said automatic selecting means for measuring the coating thickness of the test sample using the selected calibration curve.

2. Coating thickness gauge according to claim 1, further comprising a plurality of collimators having respectively different sizes, one of which is smaller than all of the other collimators, and wherein said one collimator is employed for focussing the primary X-ray beam for producing fluorescence for use by said automatic identification means.

3. A coating thickness gauge according to claim 1, further comprising a support for supporting the sample during irradiation by said means for irradiating, wherein said support is made of a light material.

4. A coating thickness gauge according to claim 3 wherein the material of said support is a plastic.

5. Coating thickness gauge according to claim 1 wherein said differentiating circuit is operative for differentiating the detected X-ray fluorescence spectrum on the basis of wavelength.

* * * * *